US00PP09458P

United States Patent [19]

van Andel

[11] Patent Number: Plant 9,458

[45] Date of Patent: Feb. 27, 1996

[54] ALSTROEMERIA VARIETY NAMED STAPIROS

[75] Inventor: Jacob van Andel, Aalsmer, Netherlands

[73] Assignee: Van Staaveren B.V., Aaslmeer, Netherlands

[21] Appl. No.: 372,432

[22] Filed: Jan. 11, 1995

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Christie, Parker & Hale

[57] ABSTRACT

A new and distinct Alstroemeria variety which is a natural mutation of the variety 'Starosello' and which differs in petal coloration.

1 Drawing Sheet

BACKGROUND OF THE INVENTION

The present invention relates to a new and distinct variety of Alstroemeria discovered as a sport of the variety seedling named 'Starosello' among my collection of cultivated Alstroemeria maintained under controlled conditions in a greenhouse at Van Staaveren B.V., Aalsmeer, The Netherlands. The varietal denomination of the new variety is 'Stapiros'.

The first act of asexual reproduction of 'Stapiros' was in Aalsmeer, The Netherlands by propagation by dividing rootstocks. Asexual reproduction through successive generations has demonstrated that the combination of characteristics as herein disclosed for 'Stapiros' are firmly fixed and retained through successive generations of asexual reproduction.

'Stapiros' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stapiros' are of a different color than the parent while maintaining the parents good growth and flowering characteristics, as herein described. The variety is a spontaneous mutant of 'Starosello' and differs from the parent mainly in the color of the petals and is similar in other respects. The inner side color of 'Starosello' petals is near 50B and the other side is near 52B, for plants grown under glass in the Netherlands.

The plant produces numerous flowering stems, which is a desirable characteristic in a cut flower variety. 'Stapiros' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustration, which shows typical flower and vegetation characteristics, with colors being as nearly true as is possible for illustrations of this type.

DETAILED DESCRIPTION OF THE NEW VARIETY

The following is a detailed description of the new variety of Alstroemeria hybrid as observed in a greenhouse in Aalsmeer, The Netherlands. Color designations indicated are in accordance with the Royal Horticultural Society Colour Chart by color plate designations.

Botanical classification:

*Family.*—Amaryllidaceae

*Genus.*—Alstroemeria sp.

*Commercial.*—Alstroemeria hybrid.

Origin: Spontaneous mutation of 'Starosello'.

Plant

Form: Bush.

Shape: Upright.

Height: About 200 cm.

Internode length: About 1–4 cm.

Growth rate: Fast; the length of time (number of days) taken from young plants (i.e. rooted rootstocks, the stage of development in which the varieties are sold) to flowering stage under commercial greenhouse conditions is 80–90 days.

Pinching required: No.

Main stem or cane length: About 175 cm.

Growth: Vigorous.

Strength: Strong.

Foliage:

*Quantity.*—Abundant.

*Number of leaves.*—About 25 to 40.

*Size of leaf.*—Length: About 10 to 16 cm. Width: About 2 to 4 cm.

*Shape of leaf.*—Elliptical.

*Margin type.*—Straight.

*Texture.*—Glossy.

*Color.*—Upper side: Near 137A. Underside: Near 137C.

*Rhizomes.*—Yes. Color: Near 155D. Size: About 10–30 cm.

Inflorescence—Flower/Floret

Blooming habit: Continuous.

Are spent umbels required to be pinched to maintain the claimed plant in a continuous blooming condition?: No.

Blooms: Profusely.

*Spring.*—Yes.

*Fall.*—Yes.

*Has tendency to give few blooms in fall.*—No.

Size: Medium.

*Diameter.*—About 5 cm.

*Depth.*—About 5 cm.

Stage when described: When first anthers release their pollen.

Borne: Singly in simple panicles.

Shape or form:

*When bloom first opens.*—Cup.
*When bloom matures.*—Cup.
Petalage:
*Number of petals.*—6.
*Arrangement.*—2 concentric circles of 3 petals.
*Form.*—Obovate.
*Margin type.*—Minutely crimped; outer petals complete.
*Apex.*—Pointed.
*How long do petals stay on stem?*—About 2 weeks.
*Texture.*—Soft.
*Appearance.*—Velvety.
*Color (summer/fall).*—Outer petal/floret: Body near 55B to 55C; base near 55B; reverse side near 55B. Inner petal/floret: Body near 55B at the base and apex suffusing gradually into a broad, central band of near 5A; reverse side near 55B to 55D in about the same zoning to near 5A.
*Spotting.*—On inner lower petals and outer petals is variable and ranges from few to no spots.
Peduncle or flower stem:
*Length.*—About 5 to 10 cm.
*Color.*—Near 137C.
*Strength.*—Strong.
*Upright.*—Yes.
*Discoloration after full bloom?*—Slightly, the main petal color, near 55B to 55C, turns to near 55C to 55D.
*Is bloom affected by wet or hot weather?*—No.
*Persistence (does flower hang on and dry?).*—No.
*Disease resistance.*—Unknown.
*Fragrance.*—None.
*Lasting quality.*—On plant: About 3 weeks. As cut flower: About 12 to 14 days.

Bud

Size:
*Diameter.*—About 1–2 cm.
*Depth or length.*—About 2–4 cm.
Form or shape: Pear-shaped.
*Long.*—Yes.
*Pointed.*—No.
Rate of opening: Fast.
Color of petals/tepals:
*When petals first divide.*—Near 55B.
*When petals begin to unfurl.*—Near 55B.
Peduncle or flower stem:
*Length.*—About 5 to 10 cm.
*Hairy.*—No.
*Strength or character.*—Erect.
*Color.*—Near 137B to 137C.

Reproductive Organs

Stamen:
*Number.*—6.
*Arrangement.*—Around the style.
Anthers:
*Size.*—About 8–10 mm.
*Color.*—Near 144B.
Filaments:
*Length.*—About 5 cm.
*Color.*—Near 54B.
Pollen:
*Color.*—Near 7A.
Pistils:
*Number.*—1.
Styles:
*Length.*—About 4–5 cm.
*Color.*—Near 54B.
Stigmas:
*Color.*—Near 54B.

FRUIT

Fertile: No.
Shape: Round.
Colored maturity: Near 163A.

I claim:

1. A new variety of Alstroemeria substantially as herein shown and described.

* * * * *

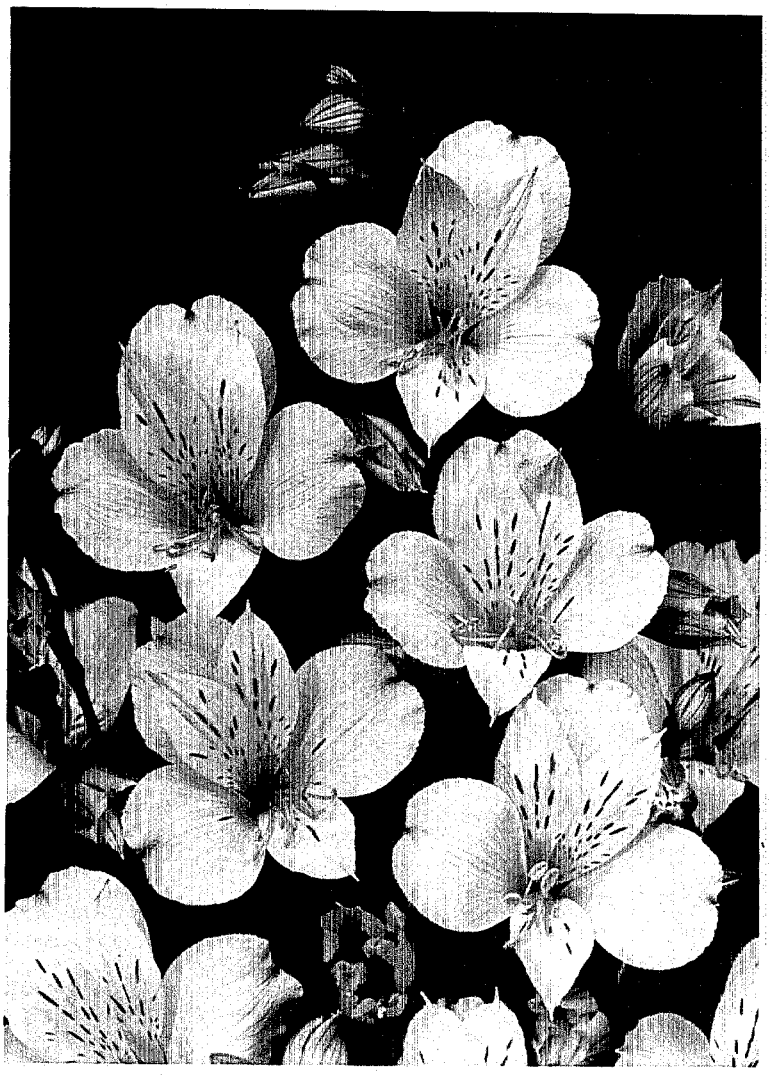

UNITED STATES PATENT AND TRADEMARK OFFICE

CERTIFICATE OF CORRECTION

PATENT NO. : Plant 9,458

DATED : February 27, 1996

INVENTOR(S) : Jacob van Andel

It is certified that error appears in the above-indentified patent and that said Letters Patent is hereby corrected as shown below:

Column 1, line 30, change "other" to -- outer --.

Column 3, delete lines 13-18 and insert therefor

-- *Color (summer/fall)*.— Outer petal/floret: Body near 55B at the base and apex suffusing gradually into a broad, central band of near 5A; reverse side near 55B to 55D in about the same zoning. Inner petal/floret: Body near 55B to near 5A; base near 55B; reverse side near 55B to near 5A. --

Signed and Sealed this

Eleventh Day of June, 1996

*Attest:*

*Attesting Officer*

BRUCE LEHMAN

*Commissioner of Patents and Trademarks*